United States Patent
Williams

(10) Patent No.: US 11,540,827 B2
(45) Date of Patent: Jan. 3, 2023

(54) HAND-HELD ELECTROMECHANICAL SURGICAL INSTRUMENTS

(71) Applicant: Covidien LP, Mansfield, MA (US)

(72) Inventor: Justin Williams, Southbury, CT (US)

(73) Assignee: COVIDIEN LP, Mansfield, MA (US)

(*) Notice: Subject to any disclaimer, the term of this patent is extended or adjusted under 35 U.S.C. 154(b) by 115 days.

(21) Appl. No.: 17/099,936

(22) Filed: Nov. 17, 2020

(65) Prior Publication Data

US 2021/0177407 A1 Jun. 17, 2021

Related U.S. Application Data

(60) Provisional application No. 62/947,805, filed on Dec. 13, 2019.

(51) Int. Cl.
*A61B 17/072* (2006.01)
*A61B 17/068* (2006.01)
*A61B 17/00* (2006.01)

(52) U.S. Cl.
CPC ...... *A61B 17/0686* (2013.01); *A61B 2017/00398* (2013.01); *A61B 2017/00407* (2013.01)

(58) Field of Classification Search
CPC .. A61B 2017/00367; A61B 2017/00407; A61B 17/07207
See application file for complete search history.

(56) References Cited

U.S. PATENT DOCUMENTS

| | | | |
|---|---|---|---|
| 4,196,348 A | 4/1980 | Iwakiri et al. | |
| 4,803,362 A | 2/1989 | Butts | |
| 5,321,311 A | 6/1994 | Umemura et al. | |
| 5,597,107 A * | 1/1997 | Knodel | A61B 17/07207 227/176.1 |
| 5,747,953 A | 5/1998 | Philipp | |
| 6,013,991 A | 1/2000 | Philipp | |
| 6,025,683 A | 2/2000 | Philipp | |
| 6,517,565 B1 | 2/2003 | Whitman et al. | |
| 6,755,338 B2 * | 6/2004 | Hahnen | A61B 17/07207 227/19 |
| 6,960,894 B2 | 11/2005 | Carusillo et al. | |
| 7,303,108 B2 * | 12/2007 | Shelton, IV | A61B 17/0682 227/176.1 |

(Continued)

FOREIGN PATENT DOCUMENTS

| | | |
|---|---|---|
| CN | 101227187 A | 7/2008 |
| CN | 203014768 U | 6/2013 |

(Continued)

OTHER PUBLICATIONS

European Search Report dated Jun. 21, 2021, issued in corresponding EP Appln. No. 20213417, 10 pages.

(Continued)

*Primary Examiner* — Gloria R Weeks
(74) *Attorney, Agent, or Firm* — Carter, DeLuca & Farrell LLP

(57) ABSTRACT

A handle assembly of a hand-held surgical instrument includes a motor and an actuation trigger. Clamping and/or stapling tissue may be carried out by actuation of the trigger. The motor may be activated to assist the manual actuation of the trigger. The handle assembly may include distinct gears for effecting discrete functions of an attached end effector.

22 Claims, 14 Drawing Sheets

(56) References Cited

U.S. PATENT DOCUMENTS

| | | | |
|---|---|---|---|
| 7,357,287 B2* | 4/2008 | Shelton, IV | A61B 17/07207 227/19 |
| 7,638,958 B2 | 12/2009 | Philipp et al. | |
| 8,080,004 B2* | 12/2011 | Downey | A61B 17/2909 606/1 |
| 8,480,703 B2 | 7/2013 | Nicholas et al. | |
| 8,968,276 B2 | 3/2015 | Zemlok et al. | |
| 9,307,986 B2 | 4/2016 | Hall et al. | |
| 9,326,767 B2 | 5/2016 | Koch, Jr. et al. | |
| 9,398,911 B2 | 7/2016 | Auld | |
| 9,468,438 B2 | 10/2016 | Baber et al. | |
| 9,554,794 B2 | 1/2017 | Baber et al. | |
| 9,597,104 B2 | 3/2017 | Nicholas et al. | |
| 9,654,050 B2 | 5/2017 | Kokinelis et al. | |
| 9,700,309 B2 | 7/2017 | Jaworek et al. | |
| 9,700,318 B2 | 7/2017 | Scirica et al. | |
| 9,775,610 B2 | 10/2017 | Nicholas et al. | |
| 9,782,169 B2 | 10/2017 | Kimsey et al. | |
| 9,782,187 B2 | 10/2017 | Zergiebel et al. | |
| 9,801,646 B2 | 10/2017 | Zergiebel et al. | |
| 9,991,069 B2 | 6/2018 | Nicholas et al. | |
| 11,090,097 B2* | 8/2021 | Reed | A61B 17/8872 |
| 2006/0000867 A1* | 1/2006 | Shelton, IV | A61B 17/07207 227/19 |
| 2007/0093790 A1* | 4/2007 | Downey | A61B 17/2909 606/1 |
| 2007/0194079 A1* | 8/2007 | Hueil | B25C 5/0292 227/176.1 |
| 2008/0035701 A1 | 2/2008 | Racenet et al. | |
| 2009/0095790 A1 | 4/2009 | Whitman et al. | |
| 2010/0038403 A1* | 2/2010 | D'Arcangelo | A61B 17/072 227/176.1 |
| 2010/0171026 A1 | 7/2010 | Saitou et al. | |
| 2011/0121049 A1 | 5/2011 | Malinouskas et al. | |
| 2011/0204119 A1 | 8/2011 | McCuen | |
| 2012/0089131 A1 | 4/2012 | Zemlok et al. | |
| 2012/0130420 A1 | 5/2012 | Nicholas et al. | |
| 2012/0253329 A1 | 10/2012 | Zemlok et al. | |
| 2012/0296159 A1 | 11/2012 | Kanazawa et al. | |
| 2012/0296316 A1 | 11/2012 | Imuta | |
| 2012/0298720 A1 | 11/2012 | Marczyk | |
| 2013/0184730 A1 | 7/2013 | Beardsley et al. | |
| 2013/0319706 A1 | 12/2013 | Nicholas et al. | |
| 2013/0324979 A1 | 12/2013 | Nicholas et al. | |
| 2014/0012238 A1 | 1/2014 | Chen et al. | |
| 2014/0114403 A1 | 4/2014 | Dale et al. | |
| 2014/0246477 A1 | 9/2014 | Koch, Jr. et al. | |
| 2014/0246479 A1 | 9/2014 | Baber et al. | |
| 2014/0249557 A1 | 9/2014 | Koch, Jr. et al. | |
| 2014/0299647 A1 | 10/2014 | Scirica et al. | |
| 2014/0303668 A1 | 10/2014 | Nicholas et al. | |
| 2014/0358129 A1 | 12/2014 | Zergiebel et al. | |
| 2015/0235789 A1 | 8/2015 | Calderoni | |
| 2015/0374372 A1 | 12/2015 | Zergiebel et al. | |
| 2017/0245854 A1 | 8/2017 | Zemlok et al. | |
| 2019/0038283 A1 | 2/2019 | Shelton, IV et al. | |

FOREIGN PATENT DOCUMENTS

| | | |
|---|---|---|
| EP | 2055243 B1 | 8/2011 |
| EP | 2777539 A2 | 9/2014 |
| EP | 2455007 B1 | 4/2016 |
| EP | 3011910 B1 | 11/2017 |
| KR | 20020020332 A | 3/2002 |
| KR | 20070000199 A | 1/2007 |
| WO | 2008147415 A1 | 12/2008 |
| WO | 2017123837 A2 | 7/2017 |

OTHER PUBLICATIONS

European Search Report dated Oct. 23, 2019, corresponding to counterpart European Application No. 19185132.8; 14 pages.
European Search Report dated Feb. 3, 2020, corresponding to counterpart European Application No. 19185132.8; 15 pages.

* cited by examiner

HAND-HELD ELECTROMECHANICAL SURGICAL INSTRUMENTS

CROSS-REFERENCE TO RELATED APPLICATIONS

This application claims the benefit of and priority to U.S. Provisional Patent Application Ser. No. 62/947,805 filed Dec. 13, 2019, the entire disclosure of which is incorporated by reference herein.

BACKGROUND

1. Technical Field

The disclosure relates to surgical instruments. More specifically, the disclosure relates to hand-held electromechanical surgical instruments that articulate, rotate, and actuate a variety of other functions of surgical attachments, such as, for example, surgical end effectors.

2. Background of Related Art

Electromechanical surgical instruments include a reusable handle assembly and disposable loading units and/or single use loading units, such as, for example, surgical end effectors. The end effectors are selectively connected to the handle assembly prior to use and then disconnected from the handle assembly following use in order to be disposed of or in some instances sterilized or reconditioned for re-use. Some handle assemblies may include one or more drive mechanisms for carrying out the operational functions of the end effector.

SUMMARY

In one aspect of the disclosure, a handle assembly of a hand-held surgical instrument is provided and includes a handle housing a rack axially movable within the handle housing, a trigger movably coupled to the handle housing, a clamp gear, and a fire gear. The rack is configured to operably couple to a functional component of an end effector assembly. The rack has a bottom surface defining a first set of gear teeth and a top surface defining a second set of gear teeth. The clamp gear is coupled to the trigger and operably coupled to the first set of gear teeth of the rack, and the fire gear is coupled to the trigger and operably coupled to the second set of gear teeth.

In aspects, the handle assembly may further include a button coupled to the trigger and configured to move between a first position and a second position. In the first position, the button may non-rotationally couple the clamp gear to the trigger, such that the clamp gear rotates in response to an actuation of the trigger. In the second position, the button may non-rotationally couple the fire gear to the trigger, such that the fire gear rotates in response to an actuation of the trigger.

In aspects, the button may include a nub, and the clamp gear may define a slot in which the nub of the button is configured to be received when the button is in the first position.

In aspects, the slot may have a first section defining a first thickness, and a second section defining a second thickness, different than the first thickness.

In aspects, the fire gear may define a first slot in which the nub of the button is configured to be received when the button is in the second position.

In aspects, the fire gear may define a channel along which the nub is configured to travel. The first slot may be disposed at a first end of the channel, and the fire gear defining a second slot disposed at a second end of the channel.

In aspects, the nub of the button may move from the first position to the second position when the slot of the clamp gear is aligned with the first slot of the fire gear.

In aspects, the trigger and the fire gear may be non-rotationally coupled to one another when the nub of the button is received in the second slot of the fire gear.

In aspects, the fire gear may define an arcuate channel having a spring received therein. The trigger may have a protuberance received in the arcuate channel. The protuberance of the trigger may be configured to compress the spring in response to a movement of the trigger from an unactuated position to an actuated position.

In aspects, the spring may be configured to rotate the trigger toward the unactuated position upon the nub of the button moving from the slot of the clamp gear to the channel of the fire gear.

In aspects, the button may be resiliently biased toward the first position.

In aspects, the handle assembly may further include a compound gear having a spur gear in meshing engagement with the second set of teeth of the rack, and a pinion gear in meshing engagement with the fire gear.

In aspects, the fire gear may be a sector gear, and the clamp gear may be a spur gear in meshing engagement with the first set of teeth of the rack.

In aspects, the handle assembly may further include a motor disposed within the handle housing, and a drive gear drivingly coupled to the motor and operably coupled to the rack, such that the rack is configured to axially move in response to at least one of an activation of the motor or a manual actuation of the trigger.

In aspects, the handle assembly may further include a sensor associated with the trigger and configured to sense a manual actuation of the trigger. The motor may be configured to be activated in response to the sensor sensing the manual actuation of the trigger.

In aspects, the trigger may include a handle portion and a flange extending from the handle portion. The handle portion may be configured to deflect relative to the flange to move the sensor.

In aspects, the sensor may be a hall effector sensor attached to the handle portion or the flange. The handle assembly may further include a magnet attached to the other of the handle portion or the flange.

In aspects, the trigger may define a cutout allowing the handle portion to deflect relative to the flange.

In accordance with another aspect of the disclosure, a handle assembly of a hand-held surgical instrument is provided and includes a handle housing, a motor supported in the handle housing, a rack axially movable within the handle housing and configured to operably couple to a functional component of an end effector assembly, a drive gear drivingly coupled to the motor and operably coupled to the rack, a trigger movably coupled to the handle housing, and a sensor associated with the trigger or the handle housing and configured to sense a manual actuation of the trigger. The motor is configured to be activated in response to the sensor sensing the manual actuation of the trigger.

In aspects, the trigger may include a handle portion and a flange extending from the handle portion. The flange may be pivotably coupled to the handle housing. The handle portion may be configured to deflect relative to the flange in response to an actuation of the trigger. The sensor may be positioned to sense the deflection of the handle portion.

In aspects, the sensor may be attached to the trigger and/or may be a strain gauge or a hall effect sensor.

In aspects, the handle assembly may further include a processor in communication with the motor and the sensor. The processor may be configured to activate the motor in response to the sensor sensing an actuation of the trigger.

In aspects, the processor may be configured to deliver an amount of power to the motor commensurate with an amount the trigger deflects. The sensor may be configured to sense the amount of deflection of the trigger.

In aspects, the handle assembly may further include a sensor rod and a limit switch. The sensor rod may be configured to retract in response to coupling the end effector assembly to the handle assembly. The limit switch may be communication with the motor. The sensor rod may be configured to actuate the limit switch to turn on the motor when the end effector assembly is coupled to the handle assembly.

In aspects, the handle assembly may further include a clamp gear coupled to the trigger and operably coupled to the rack, a fire gear coupled to the trigger and operably coupled to the rack, and a button coupled to the trigger and configured to move between a first position and a second position. In the first position, the button may non-rotationally couple the clamp gear to the trigger, such that the clamp gear rotates in response to an actuation of the trigger. In the second position, the button may non-rotationally couple the fire gear to the trigger, such that the fire gear rotates in response to an actuation of the trigger.

In aspects, the rack may have a bottom surface defining a first set of gear teeth, and a top surface defining a second set of gear teeth. The clamp gear may be operably coupled to the first set of gear teeth of the rack, and the fire gear may be operably coupled to the second set of gear teeth of the rack.

In aspects, the handle assembly may further include a compound gear having a spur gear operably coupled to the drive gear and in meshing engagement with the second set of gear teeth of the rack, and a pinion gear in meshing engagement with the fire gear.

In accordance with yet another aspect of the disclosure, a hand-held surgical instrument is provided that includes a handle housing, a shaft portion extending distally from the handle housing, a motor disposed within the handle housing, a rack axially movable within the handle housing and configured to operably couple to a functional component of an end effector assembly, a drive gear drivingly coupled to the motor and operably coupled to the rack, a trigger movably coupled to the handle housing, a sensor associated with the trigger or the handle housing and configured to sense a manual actuation of the trigger, a clamp gear coupled to the trigger and operably coupled to the rack, and a fire gear coupled to the trigger and operably coupled to the drive gear and the rack. The motor may be configured to be activated in response to the sensor sensing the manual actuation of the trigger.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the disclosure are described herein with reference to the accompanying drawings, wherein.

DETAILED DESCRIPTION

Figure 1:
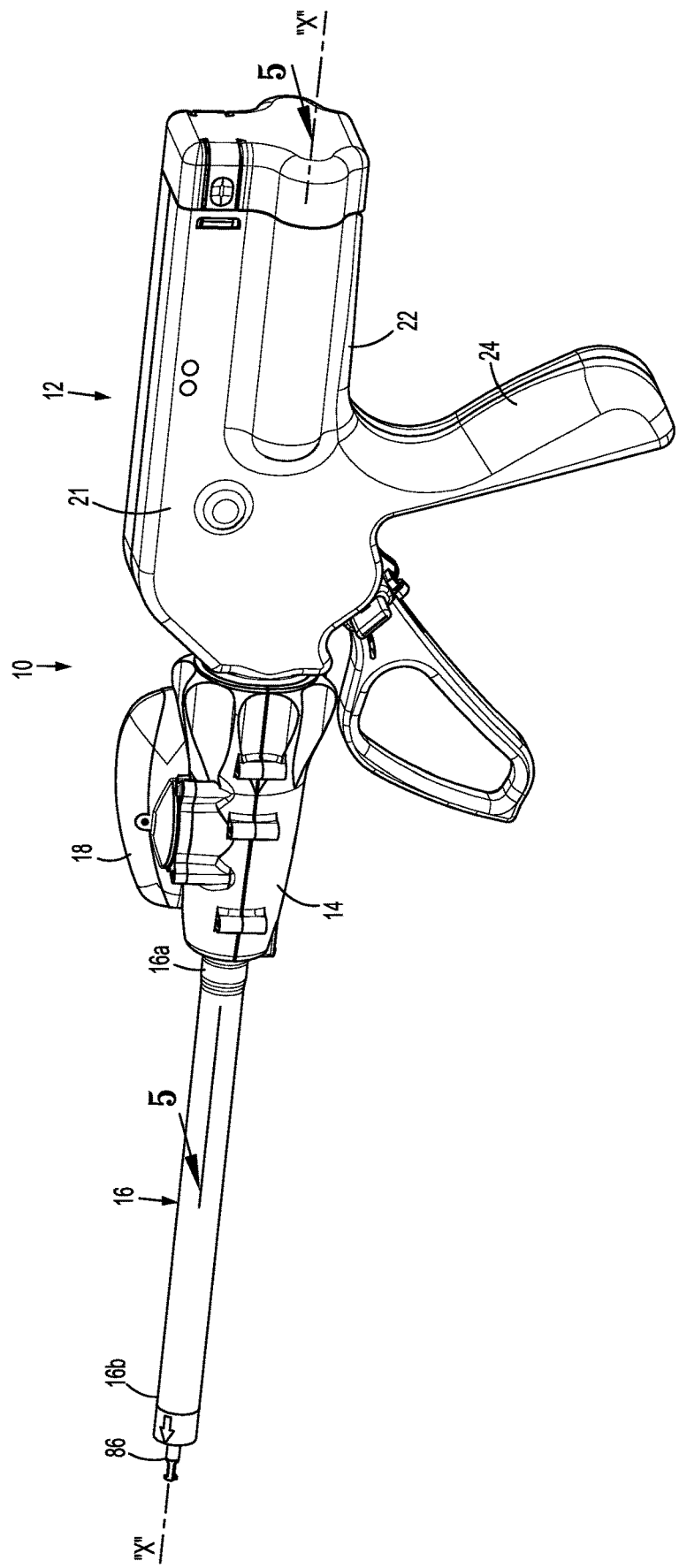
FIG. 1 is a side perspective view illustrating a hand-held electromechanical surgical instrument including a handle assembly, a knob assembly, and a shaft portion.

Embodiments of the disclosed surgical instruments are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

Figure 2:
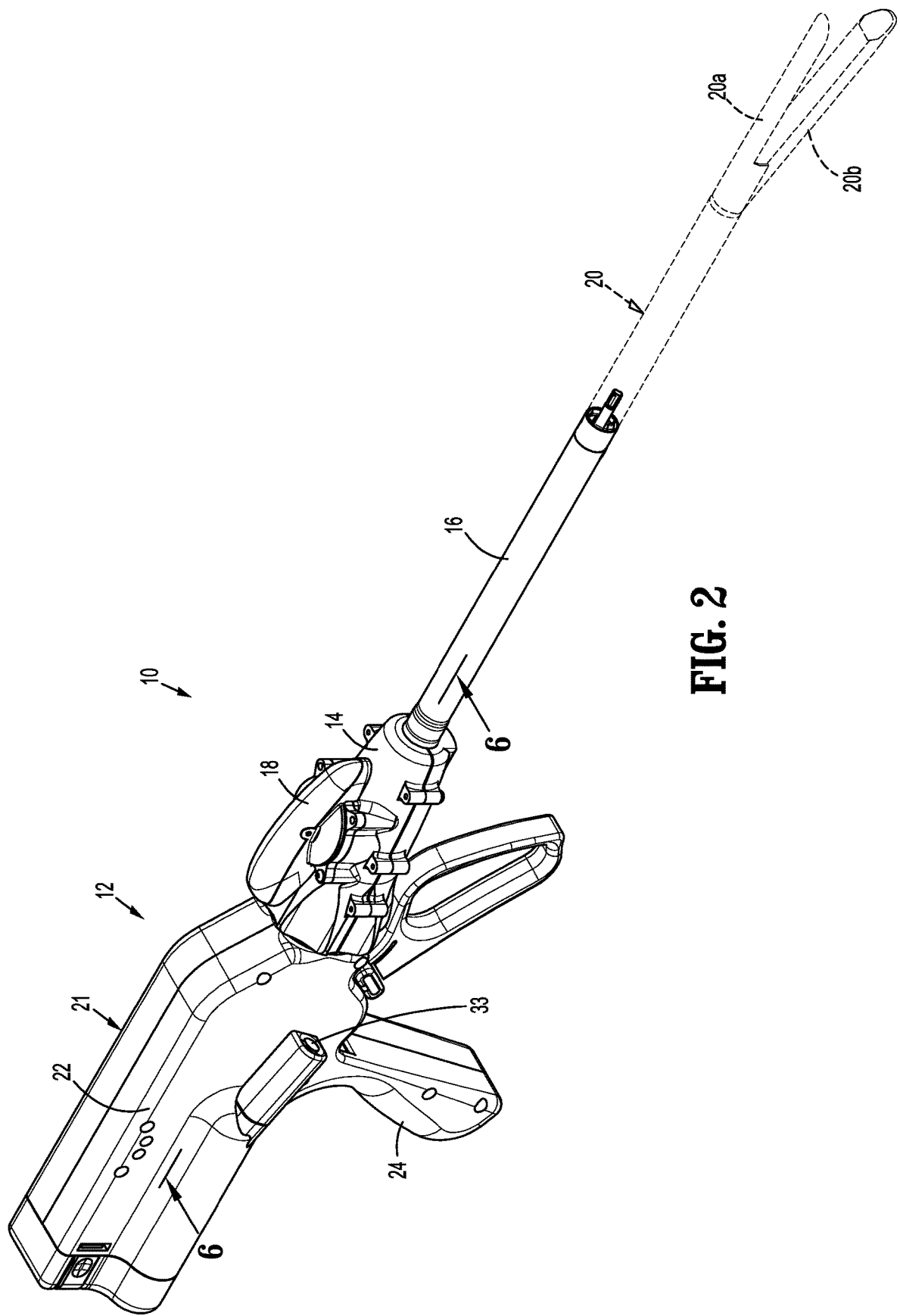
FIG. 2 is front perspective view illustrating the surgical instrument of FIG. 1 and an end effector, shown in phantom, attached thereto.

With reference to FIGS. 1 and 2, a surgical instrument, in accordance with an embodiment of the disclosure, is generally designated as 10, and is in the form of a powered hand-held electromechanical surgical instrument configured for selective coupling thereto of a plurality of different surgical end effectors, for example, a surgical stapler 20 (shown in phantom in FIG. 2). The hand-held electromechanical surgical instrument 10 includes a handle assembly 12, a knob housing 14 rotationally coupled to the handle assembly 12, and a shaft portion 16 having a proximal end portion 16a coupled to the knob housing 16 and a distal end portion 16b. The knob housing 14 is configured to be manually rotated about a longitudinal axis "X" defined by the shaft portion 16 to rotate the end effector 20 attached to the distal end portion 16b thereof. An articulation lever 18 is rotationally coupled to the knob housing 14 for actuating an articulation of the end effector 20.

With reference to FIGS. 1-3 and 7, the handle assembly 12 includes a handle housing 21 having an upper housing portion or barrel portion 22 substantially aligned with the longitudinal axis "X," and a lower housing portion or handle portion 24 extending downward and proximally from the upper housing portion 22. The handle assembly 12 includes a printed circuit board 26 extending through the lower housing portion 24, and a battery 28 (one or more batteries) and a motor 30 (e.g., a DC motor) each disposed in the upper housing portion 22. The printed circuit board 26 has a processor 32 and is configured to be in electrical communication (e.g., wirelessly or wired) with the battery 28 and the motor 30. Handle housing 21 may include a removable cap for providing access to batteries 28 and motor 30. Specifically, the cap may be located at a proximal end of handle housing 21, and may be selectively removable to permit removal and insertion of batteries 28 and motor 30 from/into handle housing 21.

The handle assembly 12 may further include a motor reverse button 33 (FIG. 2) attached to the housing portion 21. The motor reverse button 33 is in communication with the motor 30 and allows a user to directly activate the motor 30.

Figure 3:
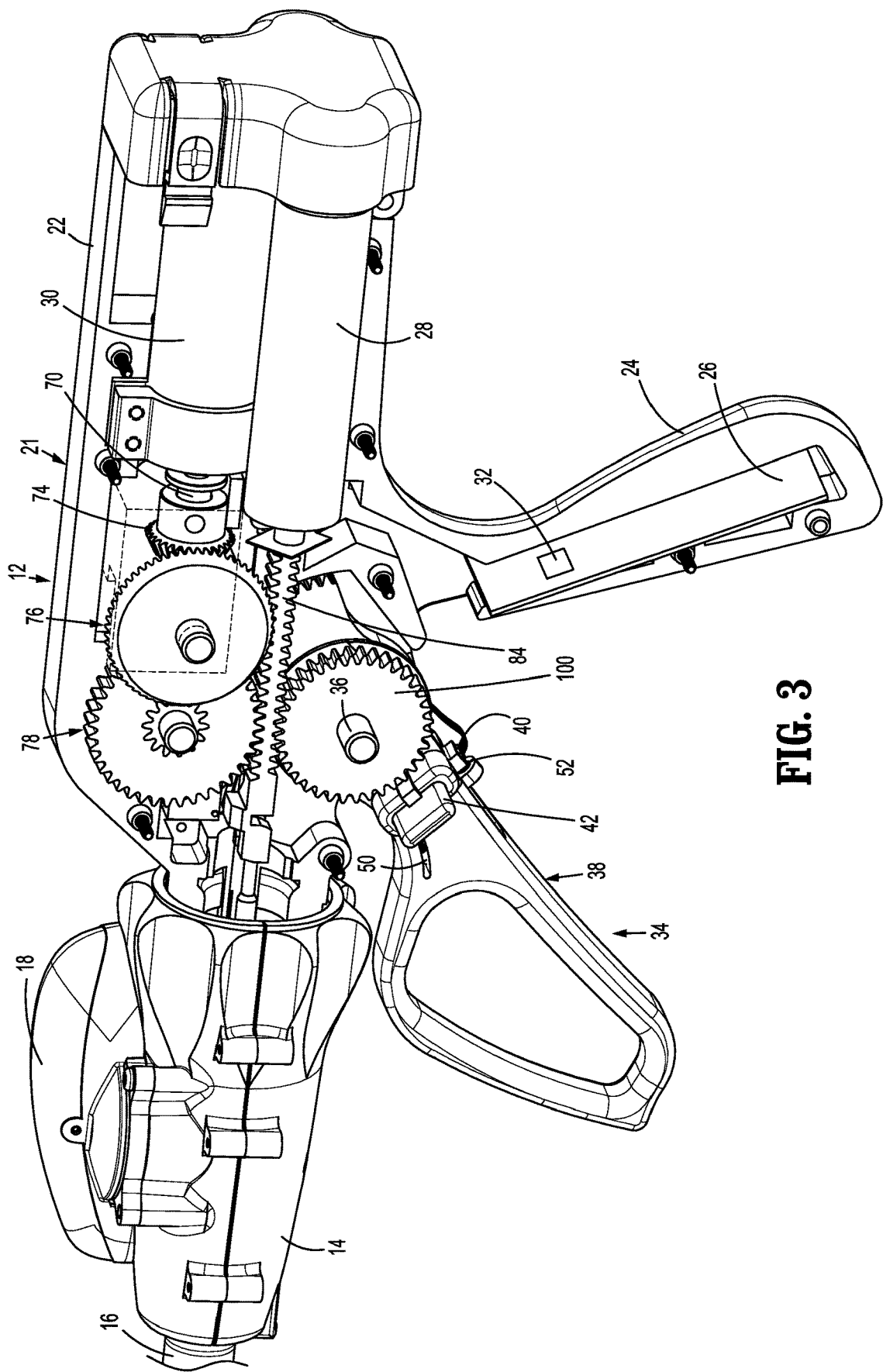
FIG. 3 is a partial side view, with a handle housing half removed, of the surgical instrument of FIG. 1 illustrating internal components of the handle assembly.
Figure 4:
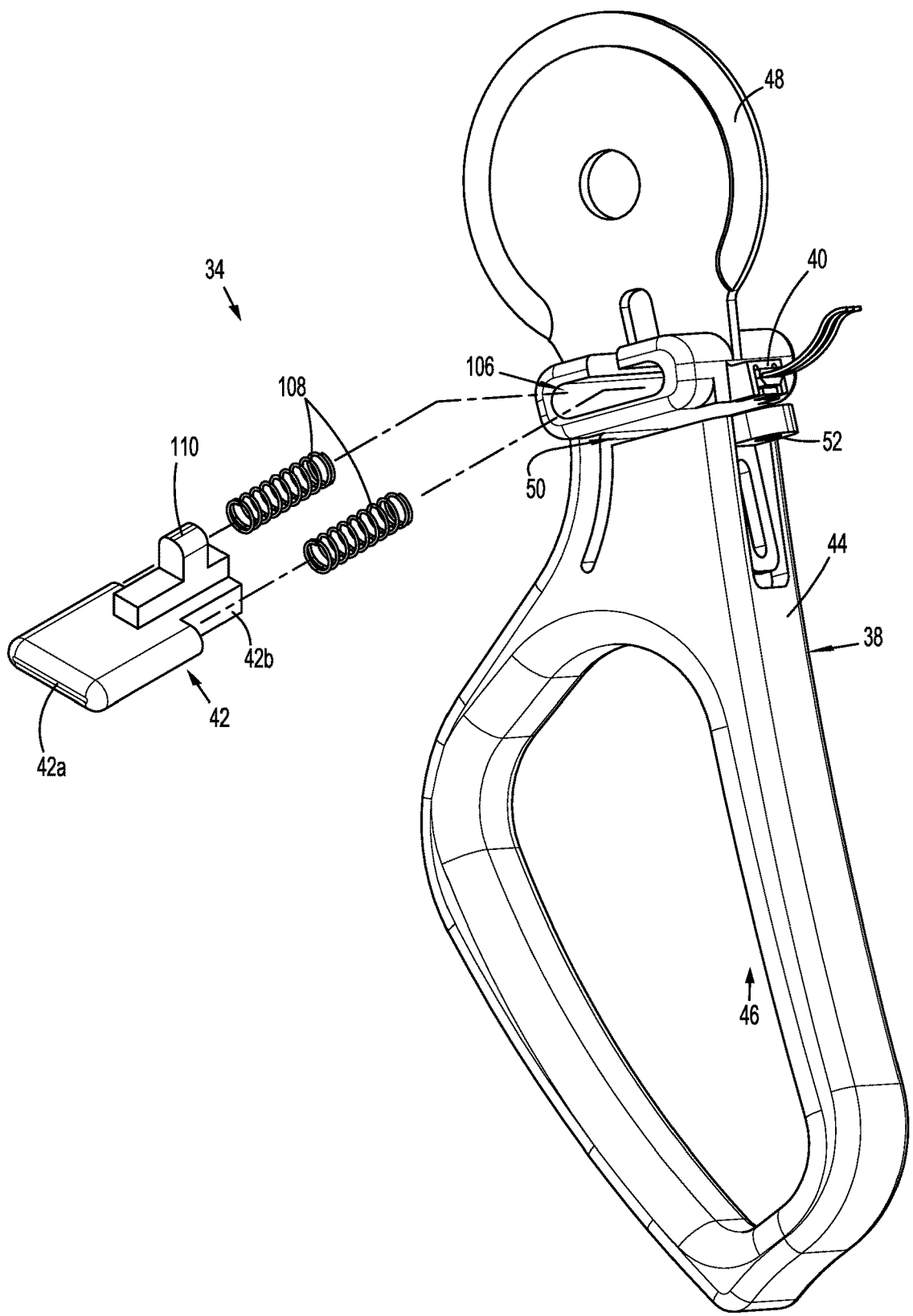
FIG. 4 is a perspective view, with parts separated, illustrating a trigger assembly of the handle assembly of FIG. 1.
Figure 7:
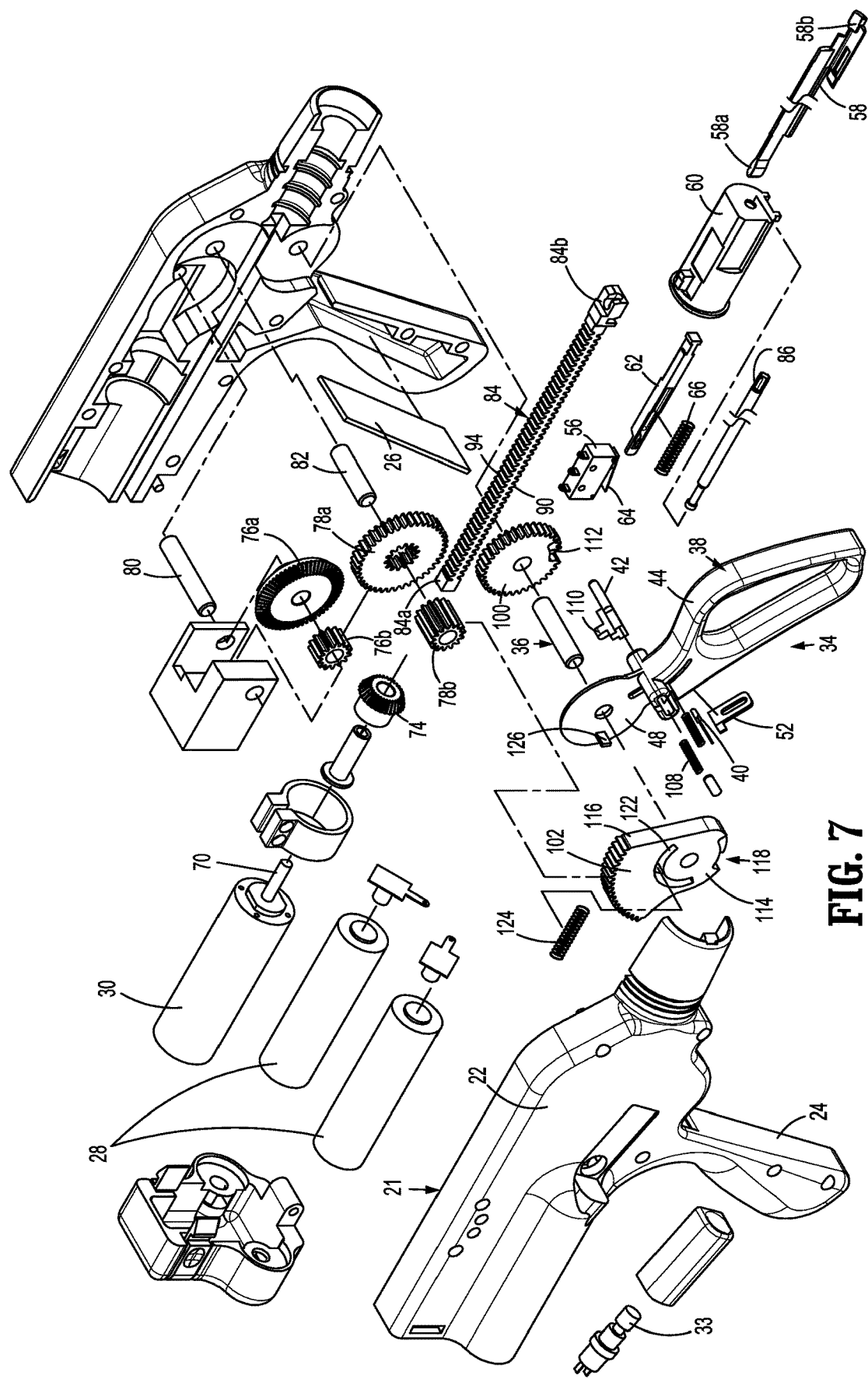
FIG. 7 is a perspective view, with parts separated, of the surgical instrument of FIG. 1.

With reference to FIGS. 3, 4, and 7, the handle assembly 12 has a trigger assembly 34 pivotably coupled to the handle housing 21 via a pivot pin 36. The trigger assembly 34 includes a hand-actuated trigger 38, a sensor 40, and a clamp/fire button 42. The trigger 38 includes a handle portion 44 defining a finger retaining opening 46, and a flange 48, such as, for example, an annular plate, extending upwardly from the handle portion 44 of the trigger 38 and pivotably coupled to the handle housing 21. The trigger 38 is mechanically coupled to the end effector 20 (FIG. 2) for transferring a mechanical actuation thereof (e.g., pivoting of the trigger 38 closer to the handle portion 24) into an actuation of the end effector 20.

The trigger 38 may be configured to induce an activation of the drive motor 30 to provide a user a motor-assisted actuation of the trigger 38. In particular, the trigger 38 defines a cutout 50 between the flange 48 and the handle portion 44 thereof that allows the handle portion 44 to deflect relative to the flange 48 upon the application of an actuation force on the trigger 38 by a user. To detect a minor deflection of the trigger 38, the trigger 38 has the sensor 40 associated therewith. For example, the sensor 40 may be a strain gauge, a hall effect sensor, or any other suitable sensor. The sensor 40 is attached to the flange 48 above the cutout 50. In aspects, the sensor 40 may be attached to the handle portion 44 below the cutout 50 or, in some aspects, attached to the handle housing portion 24. When the sensor 40 is a hall effect sensor, a magnet 52 is attached to the flange 48 of the trigger 38, such that the hall effect sensor 40 detects any changes in the distance between the hall effect sensor 40 and the magnet 52 during deflection of the trigger 38 about the cutout 50. In other aspects, instead of a cutout being provided to allow for deflection of the trigger 38, the trigger 38 may be fabricated from a suitable material allowing for flexion thereof. Further still, the trigger 38 may have a reduced thickness at a selected location to allow for deflection at the selected location.

The sensor 40 is in communication (e.g., wireless or wired) with the processor 32 (FIG. 3) and sends a signal to the processor 32 representative of a force applied to the trigger 38. The processor 32 is configured to activate the motor 30 in response to receiving, from the sensor 40, the signal indicative of a trigger 38 actuation. The processor 32 is configured to deliver, via the battery 28, an amount of power to the motor 30 commensurate with the amount the trigger 38 deflects as sensed by the sensor 40. As such, a greater force applied to the trigger 38 will result in a greater amount of power delivered to the motor 30 for actuating the end effector 20. In this way, if an actuation of the trigger 38 is met with resistance, as a product of, for example, tissue disposed between the jaw members 20a, 20b of the end effector 20, the motor 30 will be activated to assist the user in moving the trigger 38, as will be described in further detail below.

Figure 5:
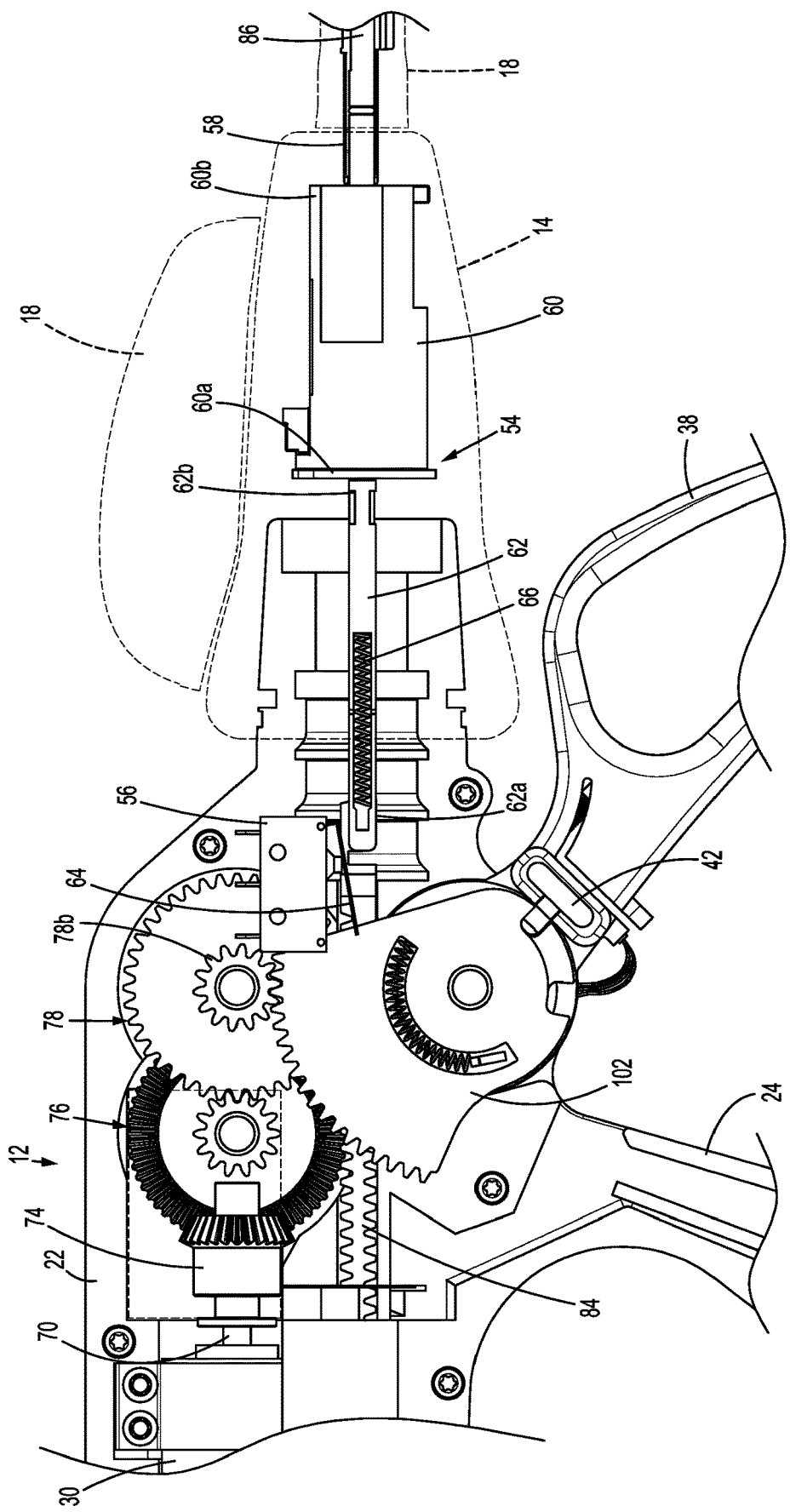
FIG. 5 illustrates a cross-section, taken along line 5-5 of FIG. 1, of the surgical instrument.
Figure 6:
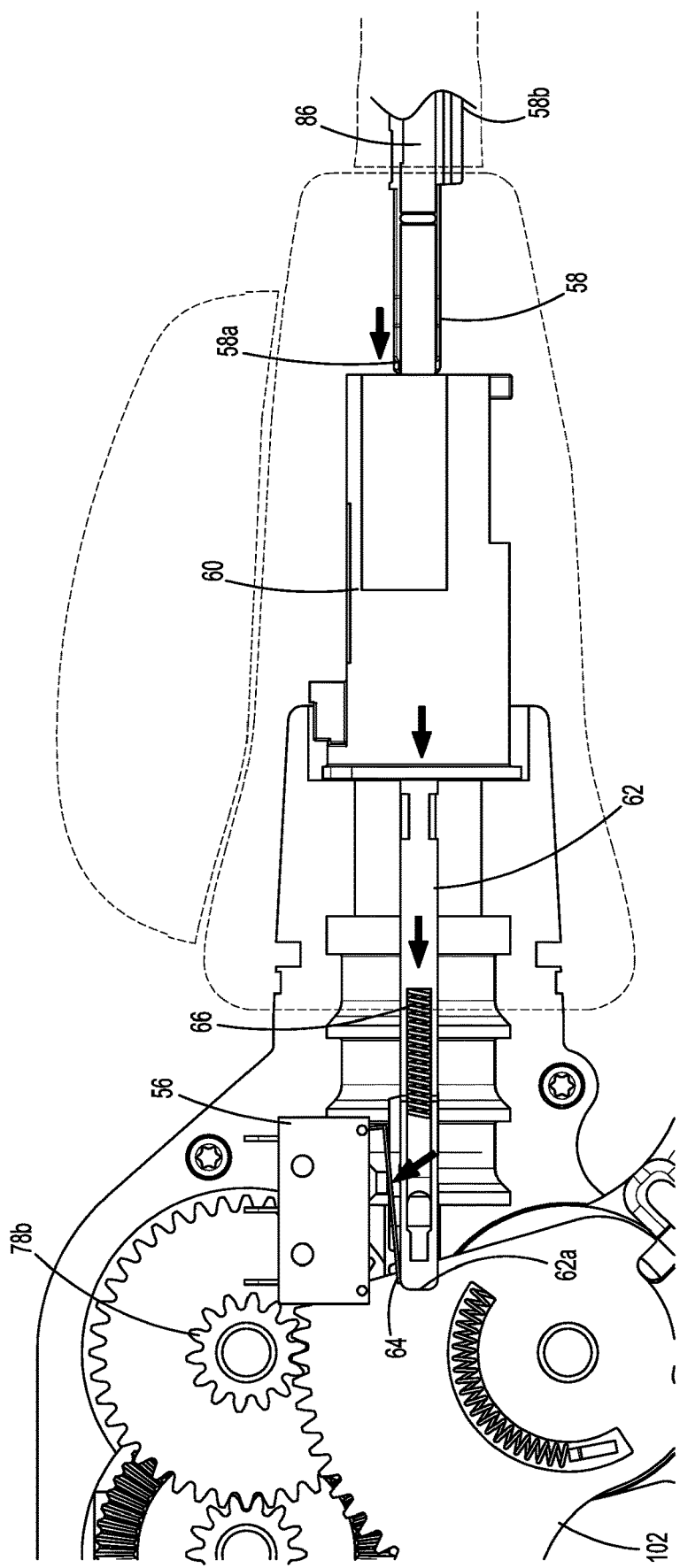
FIG. 6 illustrates a cross-section, taken along line 6-6 of FIG. 2, of the surgical instrument.

With reference to FIGS. 5-7, the handle assembly 12 further includes a sensor assembly 54 and a limit switch 56 cooperating together to enable and disable (e.g., turn off and on) the motor 30 based on whether the end effector 20 is respectively connected to or disconnected from the handle assembly 12 to save power and/or maintain the position of internal components of the handle assembly 12. The sensor assembly 54 includes an installation sensor rod 58, a sensor block 60, and a plunger 62. The limit switch 56 is in electrical communication with the motor 30 and has a lever 64 positioned for actuation by the plunger 62. The sensor rod 58 extends longitudinally through the shaft portion 16 and has a distal end portion 58b configured to be engaged by a connecting portion of the end effector 20 upon insertion of the end effector 20 into the distal end portion 16b of the shaft portion 16. A proximal end portion 58a of the sensor rod 58 is attached to a distal end portion 60b of the sensor block 60, and a distal end portion 62b of the plunger 62 is attached to a proximal end portion 60a of the sensor block 60, such that the sensor rod 58, the sensor block 60, and the plunger 62 move axially as an integral unit within the rotation knob 14.

The plunger 62 has a spring 66 disposed therein that is fixed at a proximal end to the handle housing 21. The spring 66 is configured to resiliently bias the sensing assembly 54 toward a distal position, in which the distal end portion 58b of the sensor rod 58 is positioned for engagement with the connecting portion of the end effector 20. In use, upon coupling the end effector 20 to the shaft portion 16, the sensor assembly 54 is retracted, whereby the proximal end portion 62a of the plunger 62 pivots the lever 64 of the limit switch 56 to change the status of the motor 30 from off to on.

With reference to FIGS. 7-10, the motor 30 of the handle assembly 12 is drivingly coupled to a drive shaft 70 that transmits forces generated by the motor 30 into mechanical output. The drive shaft 70 is operably coupled to the end effector 20 (FIG. 2) via a transmission assembly 72, such that rotation of the drive shaft 70 results in a closing of the jaw members 20a, 20b of the end effector 20 and ultimately the firing of staples from the end effector 20.

The transmission assembly 72 includes a small diameter bevel gear 74 non-rotationally supported by the drive shaft 70, a first compound gear 76 coupled to the small diameter bevel gear 74, and a second compound gear 78 coupled to the first compound gear 76. The first compound gear 76 is rotatably supported in the handle housing 21 via a pivot pin 80 and has a large diameter bevel gear 76a in meshing engagement with the small diameter bevel gear 74, and a pinion gear 76b fixed to the large diameter bevel gear 76a. The second compound gear 78 is disposed distally of the first compound gear 76 and is rotationally supported in the handle housing 21 via a pivot pin 82. The second compound gear 78 includes a spur gear 78a, and a pinion gear 78b fixed to the spur gear 78a. The spur gear 78a of the second compound gear 78 is in meshing engagement with the pinion gear 76b of the first compound gear 76. The spur gear 78a of the second compound gear 78 is also in meshing engagement with a rack 84.

The rack 84 extends longitudinally through the barrel portion 22 of the handle housing 21 and has a proximal end portion 84a, and a distal end portion 84b fixed with a proximal end portion of a drive rod 86, such that axial movement of the rack 84 results in a corresponding axial movement of the drive rod 86. The proximal end portion 84a of the rack 84 has a bottom surface 88 defining a plurality of gear teeth 90 along its length, and a top surface 92 defining a plurality of gear teeth 94 along its length. The gear teeth 94 of the top surface 92 are in meshing engagement with the spur gear 78a of the second compound gear 78. As such, an activation of the motor 30 effects a translation of the rack 84 via the transmission assembly 72. The gear teeth 90 of the bottom surface 88 are in meshing engagement with a clamp gear 100. As such, an activation of the motor 30 effects a rotation of the clamp gear 100 via the rack 84.

In addition to the rack 84 being mechanically drivable by the motor 30 via the transmission assembly 72, the rack 84 is also mechanically drivable by the trigger 38 via two discrete gears; the clamp gear 100 and a fire gear 102. The clamp and fire gears 100, 102 are both rotationally supported on the flange 48 of the trigger 38 by the pivot pin 36, which extends through each of the clamp and fire gears 100, 102. The clamp gear 100 may be disposed on a left-hand side of the flange 48, whereas the fire gear 102 may be disposed on a right-hand side of the flange 48. Each of the clamp and fire gears 100, 102 may be selectively rotationally fixed to the trigger 38 by the clamp/fire switch or button 42, as will be described in detail below.

Figure 9:
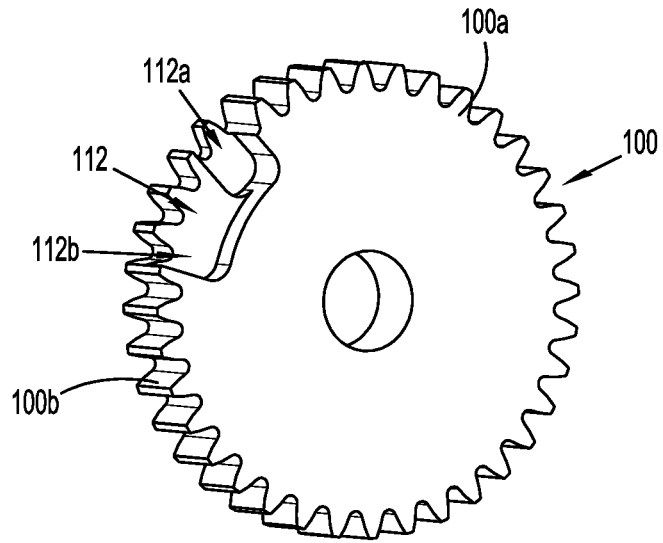
FIG. 9 is a perspective view illustrating a clamp gear of the handle assembly of FIG. 1.
Figure 11:
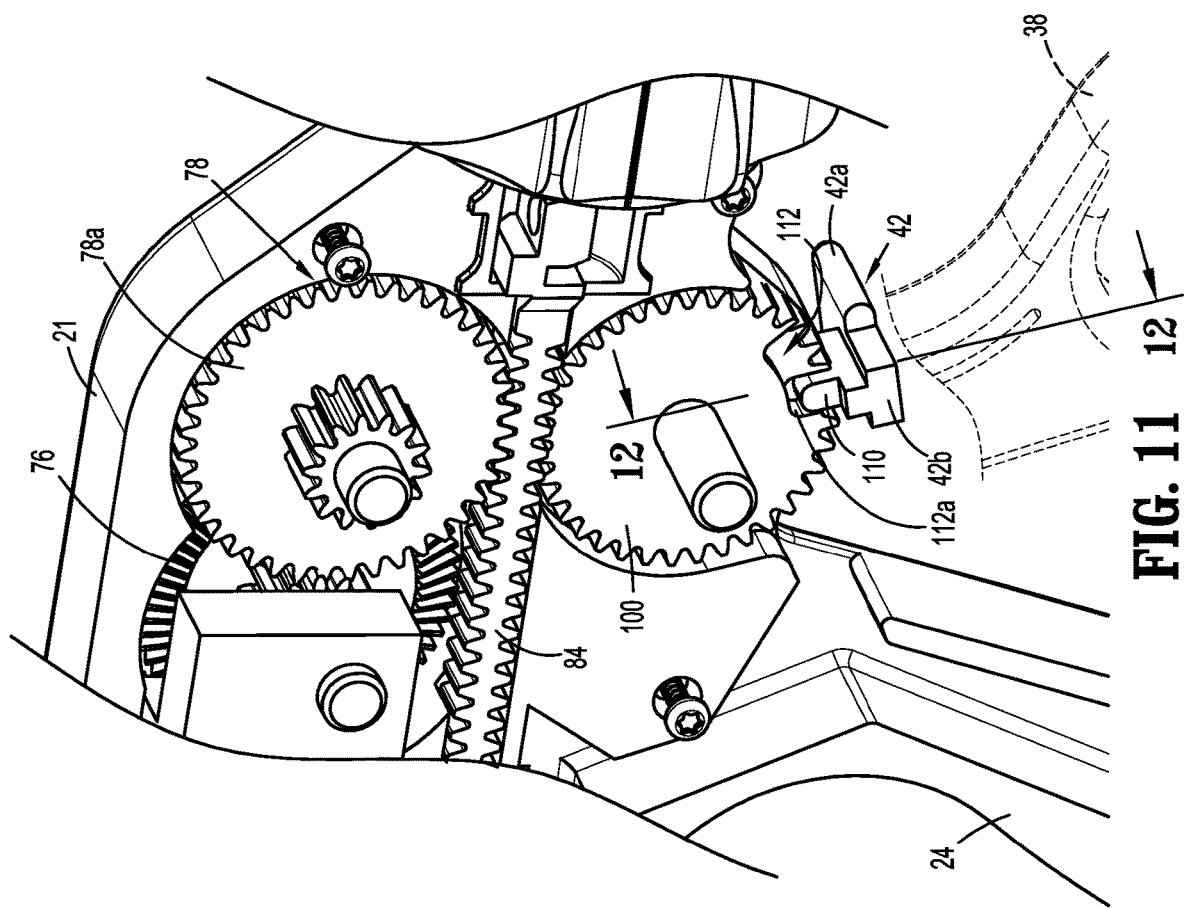
FIG. 11 is a perspective view illustrating internal components of the handle assembly of FIG. 1 in a clamping state.

With reference to FIGS. 7, 9, and 11, the clamp gear 100 may be a spur gear and is in meshing engagement with the set of gear teeth 90 on the bottom surface 88 of the rack 84. As such, axial movement of the rack 84 results in a rotation of the clamp gear 100, and rotation of the clamp gear 100 results in axial movement of the rack 84. The clamp gear 100 defines a slot 112 in a right radial side 100a thereof configured for receipt of a nub 110 (FIG. 4) of the button 42 when the button 42 is in the left position. The slot 112 in the clamp gear 100 has a first or proximal section 112a, and a second or distal section 112b continuous with and longer than the proximal section 112a. The proximal and distal sections 112a, 112b each have a different thickness as measured from the right radial side 100a of the clamp gear 100 to the left radial side 100b of the clamp gear 100. The thickness of the proximal section 112a of the slot 112 is greater than the thickness of the distal section 112b of the slot 112.

Figure 8:
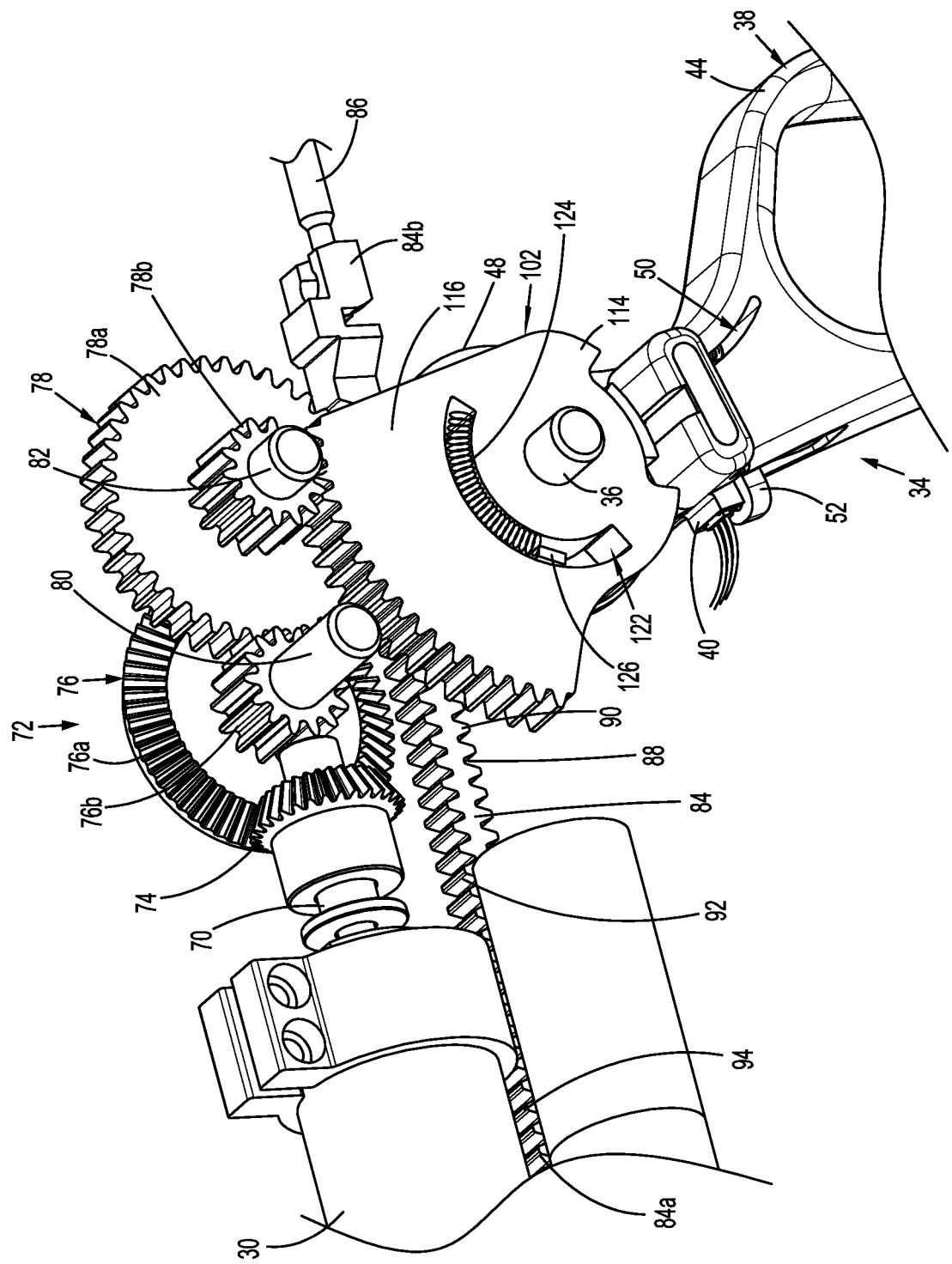
FIG. 8 is a partial perspective view illustrating internal components of the handle assembly of FIG. 1.
Figure 10:
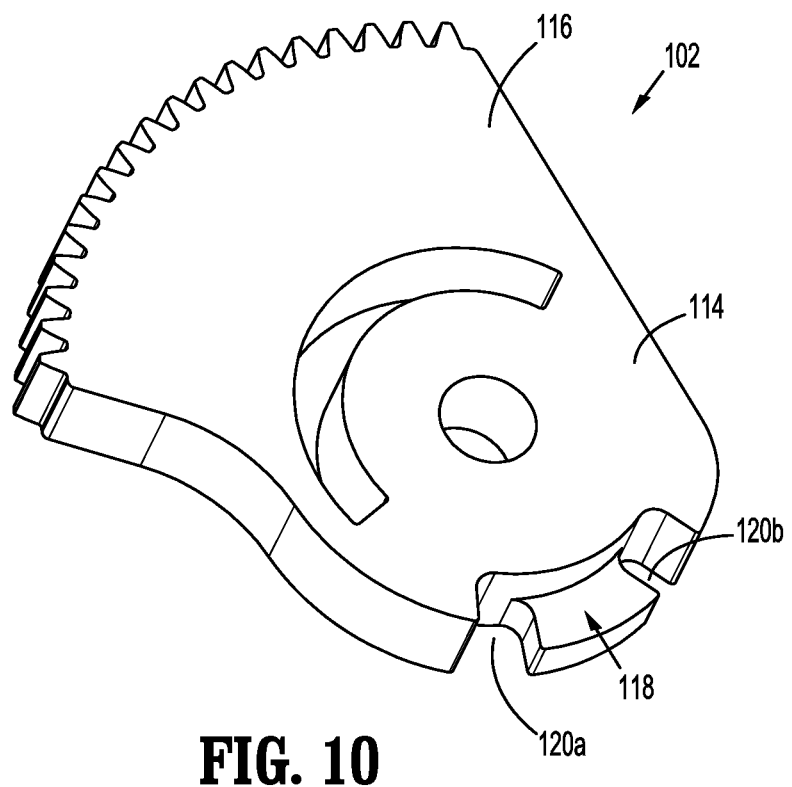
FIG. 10 is a perspective view illustrating a fire gear of the handle assembly of FIG. 1.

With reference to FIGS. 7, 8, and 10, the fire gear 102 may be a sector gear having a body portion 114 and a flared extension 116 extending upwardly from the body portion 114. The flared extension 116 of the fire gear 102 defines a plurality of gear teeth in meshing engagement with the pinion gear 78b of the second compound gear 78. As such, a rotation of the fire gear 102 results in axial movement of the rack 84 via the second compound gear 78, and axial movement of the rack 84 results in a rotation of the fire gear 102 via the second compound gear 78. The body portion 114 of the fire gear 102 defines a channel 118 in a right radial side thereof configured for receipt of the nub 110 of the button 42 when the button 42 is in the right position. The body portion 114 further defines a first slot 120a and a second slot 120b transversely therethrough and in communication with opposite proximal and distal ends of the channel 118, respectively. The first slot 120a of the fire gear 102 is configured to align with the slot 112 of the clamp gear 100 to allow the nub 110 (FIG. 4) of the button 42 to pass from the slot 112 of the clamp gear 100 and into the channel 118 of the fire gear 102. The second slot 120b of the fire gear 102 is configured to capture the nub 110 therein, upon which, rotation of the trigger 38 drives a concomitant rotation of the fire gear 102.

The fire gear 102 further defines an arcuate channel 122 in the body portion 114 thereof having a spring 124 received therein. The flange 48 of the trigger 38 has a protuberance 126 extending laterally into the arcuate channel 122 of the fire gear 102 and in abutment with an end of the spring 124. The protuberance 126 of the trigger 38 is configured to compress the spring 124 in response to a rotation of the trigger 38 relative to the fire gear 102 during a clamping of the end effector 20.

With reference to FIGS. 4, 7, and 11, the button 42 of the trigger assembly 34 is received in an aperture 106 defined in the handle portion 44 of the trigger 38 and is slidable therein between a first position and a second position to selectively couple and decouple the clamp and fire gears 100, 102 to the trigger 38. The button 42 is resiliently biased toward the first position (e.g., a position closer to the clamp gear 100) by a pair of springs 108 captured within the aperture 106 of the trigger 38. The button 42 has a left end 42a protruding from the trigger 38, and a right end 42b disposed within the trigger 38. The left end 42a of the button 42 is accessible by a user to allow a user to translate the button 42 from the first position toward the second position. The right end 42b of the button 42 has a nub or boss 110 configured to engage the clamp gear 100 when the button 42 is in the first position (e.g., left position), and engage the fire gear 102 when the button 42 is in the second position (e.g., right position). Moving the button 42 between the first and second positions allows a user to change the mechanical output of the trigger 38 depending on which of the clamp or fire gears 100, 102 is being engaged.

Figure 12:
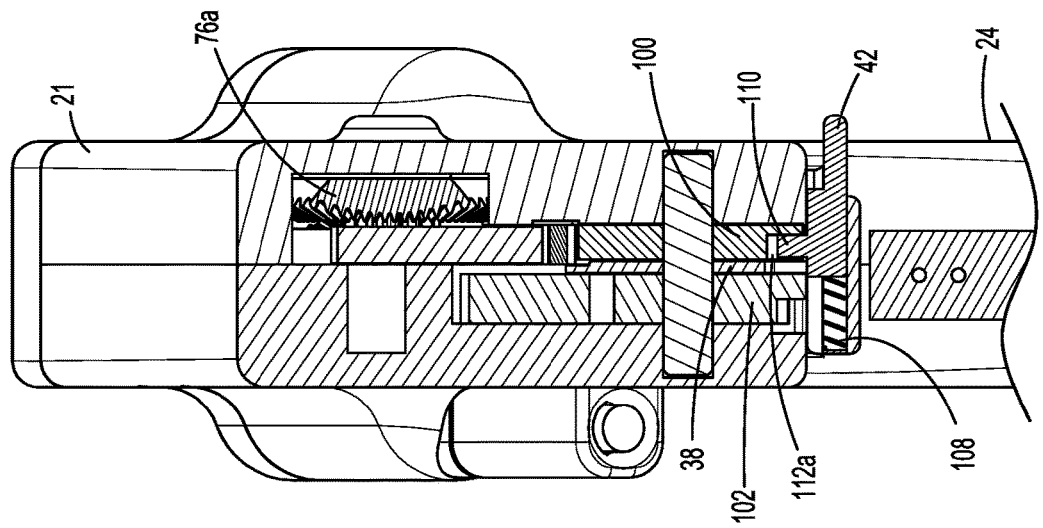
FIG. 12 illustrates a cross-section, taken along line 12-12 of FIG. 11, of the handle assembly.

With reference to FIGS. 11-18, an operation of the surgical instrument 10 will now be described. With tissue received between the jaw members 20a, 20b of the end effector 20 (FIG. 2), the trigger 38 may be actuated to drive a closing of the jaw members 20a, 20b of the end effector 20. As shown in FIGS. 11 and 12, the button 42 of the trigger assembly 34 is initially in the left or starting position, in which the nub 110 of the button 42 is received in the proximal section 112a of the slot 112 of the clamp gear 100.

Figure 13:
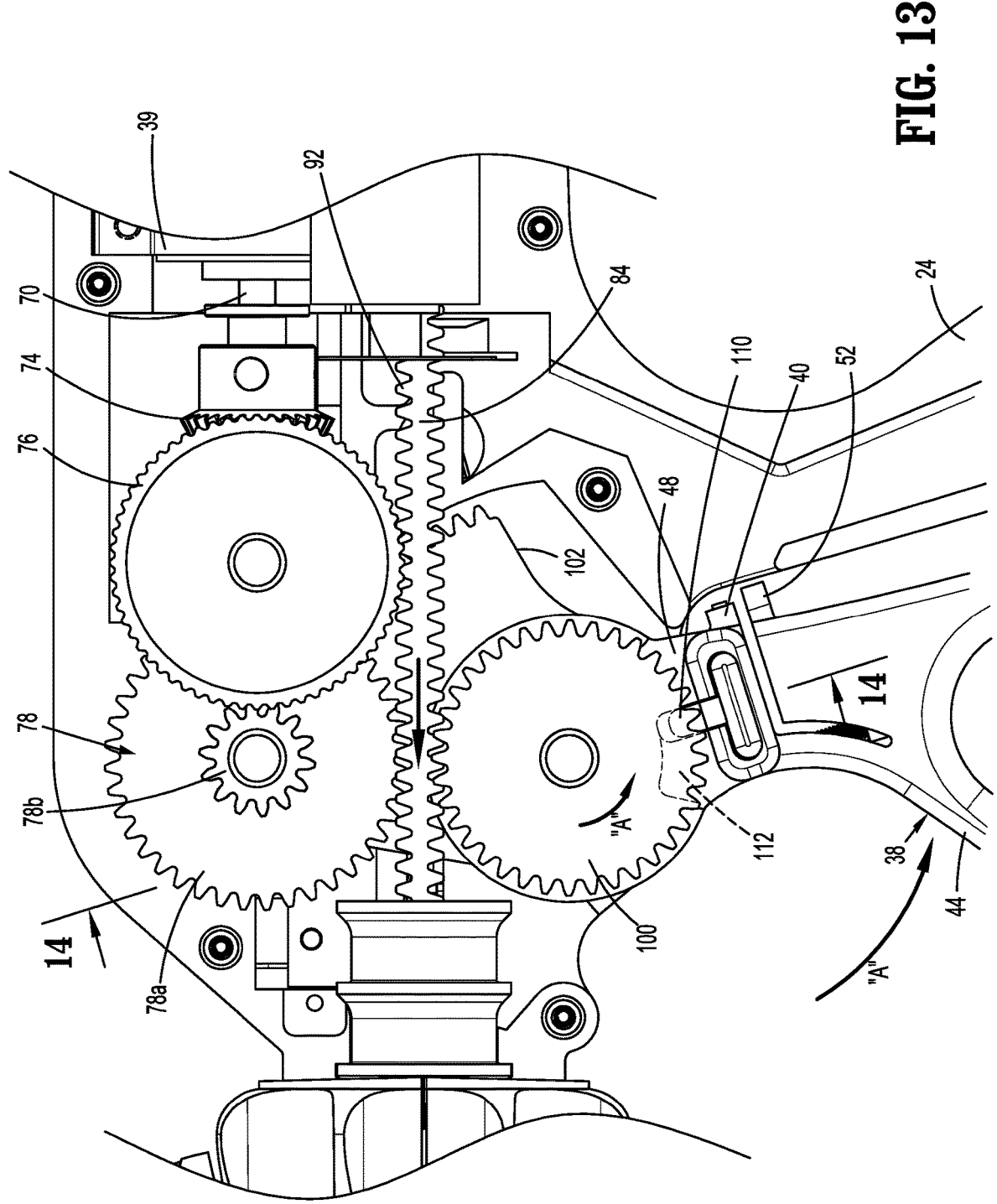
FIG. 13 is a side view illustrating internal components of the handle assembly of FIG. 1 in a clamped state.

An initial application of an actuation force on the trigger 38 by a user rotates the trigger 38 relative to the handle portion 24 of the handle housing 21, in the direction indicated by arrow "A" in FIG. 13. Due to the trigger 38 being non-rotationally fixed to the clamp gear 100 by the button 42, the clamp gear 100 rotates with the trigger 38 in the same direction. The rotation of the clamp gear 100 causes a translation (e.g., distal movement) of the rack 84 and the attached drive rod 86 to close the jaw members 20a, 20b about the tissue.

With tissue disposed between the jaw members 20a, 20b, a continued application of an actuation force on the trigger 38 may be met with some resistance. With this resistance in play, further application of an actuation force on the trigger 38 may cause the handle portion 44 of the trigger 38 to flex or deflect slightly relative to the flange 48. The sensor 40 detects the deflection of the trigger 38 and sends a signal to the processor 32 indicative of the amount of deflection sensed. The processor 32 transfers power from the battery 28 to the motor 30 in an amount that is proportional to the amount of deflection sensed by the sensor 40. For example, the greater the deflection of the trigger 38 sensed by the sensor 40 (e.g., as a result of relatively thick tissue), the more power will be delivered to the motor 30 by the processor 32 to provide the necessary motor assistance to the user.

Upon initialization of the motor assistance program of the surgical instrument 10, the drive shaft 70 rotates, which drives, in turn, a rotation of the bevel gear 74, the first compound gear 76, and the second compound gear 78. Due to the spur gear 78a of the second compound gear 78 being engaged with the top surface 92 of the rack 84, the rotation of the second compound gear 78 assists in translating the rack 84 in the desired direction. The translation of the rack 84 exerts a rotational force on the clamp gear 100 and, in turn, the trigger 38. As such, a user will experience less resistance to moving the trigger 38 with the assistance from the motor 30 and transmission assembly 72. However, the user will still experience tactile feedback due to the mechanical connection between the trigger 38 and the rack 84.

Figure 15:
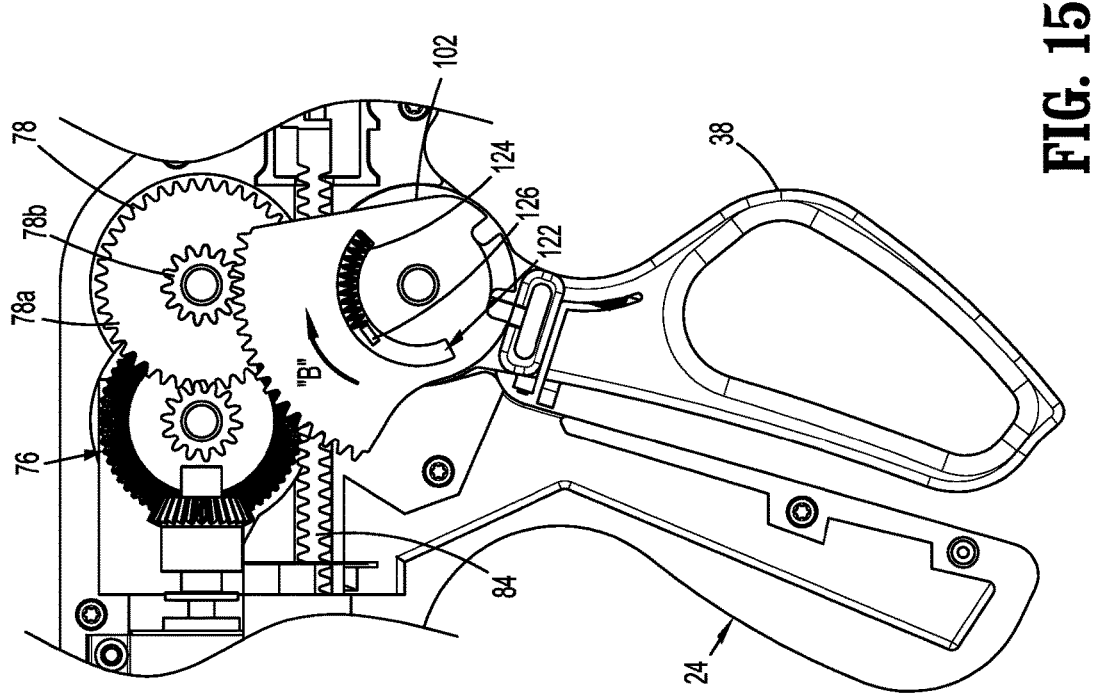
FIG. 15 is a side view illustrating internal components of the handle assembly of FIG. 1 with the trigger in a spring-loaded state.
Figure 14:
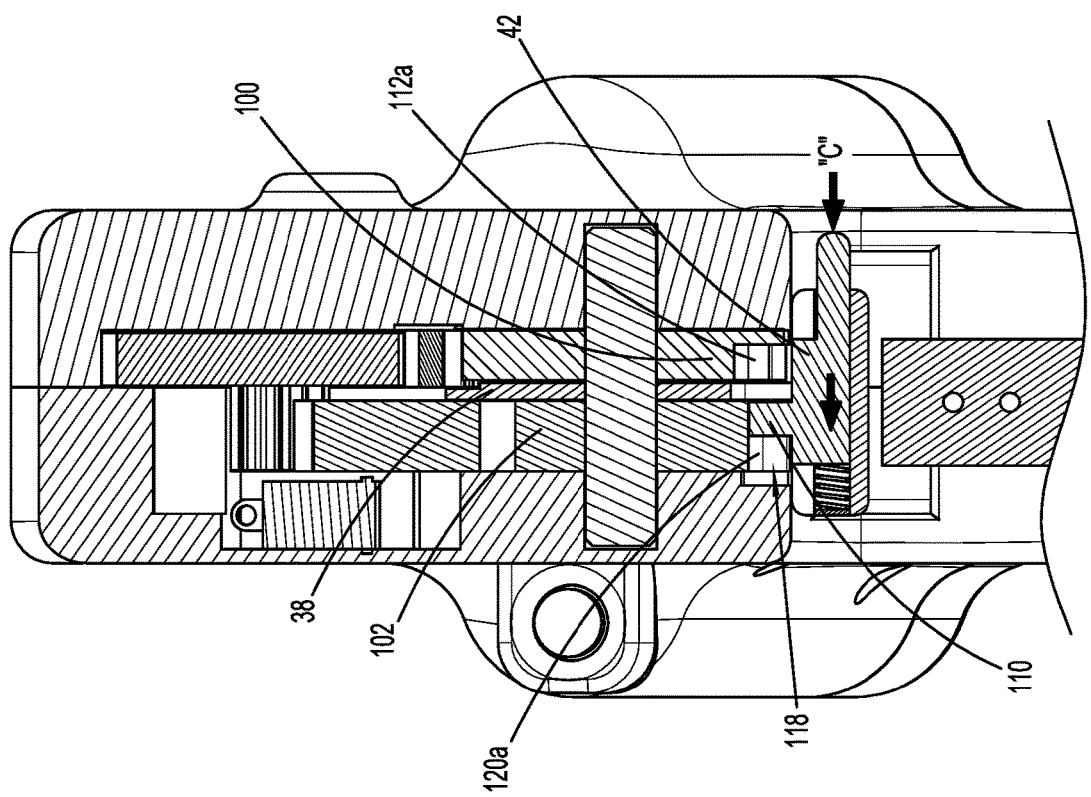
FIG. 14 illustrates a cross-section, taken along line 14-14 of FIG. 13, of the handle assembly.
Figure 17:
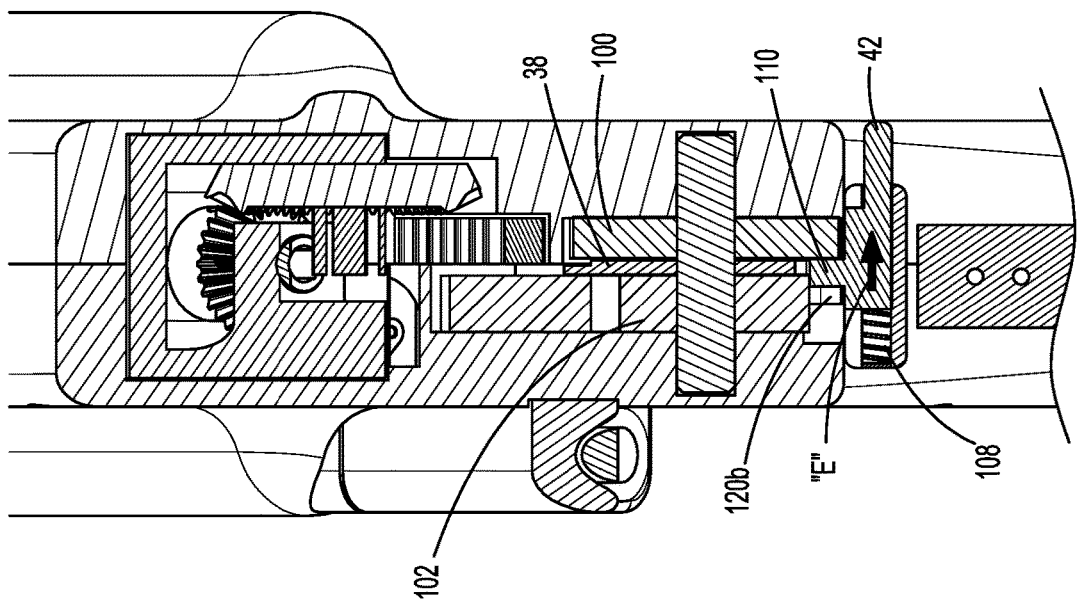
FIG. 17 illustrates a cross-section, taken along line 17-17 of FIG. 16, of the internal components of the handle assembly.
Figure 16:
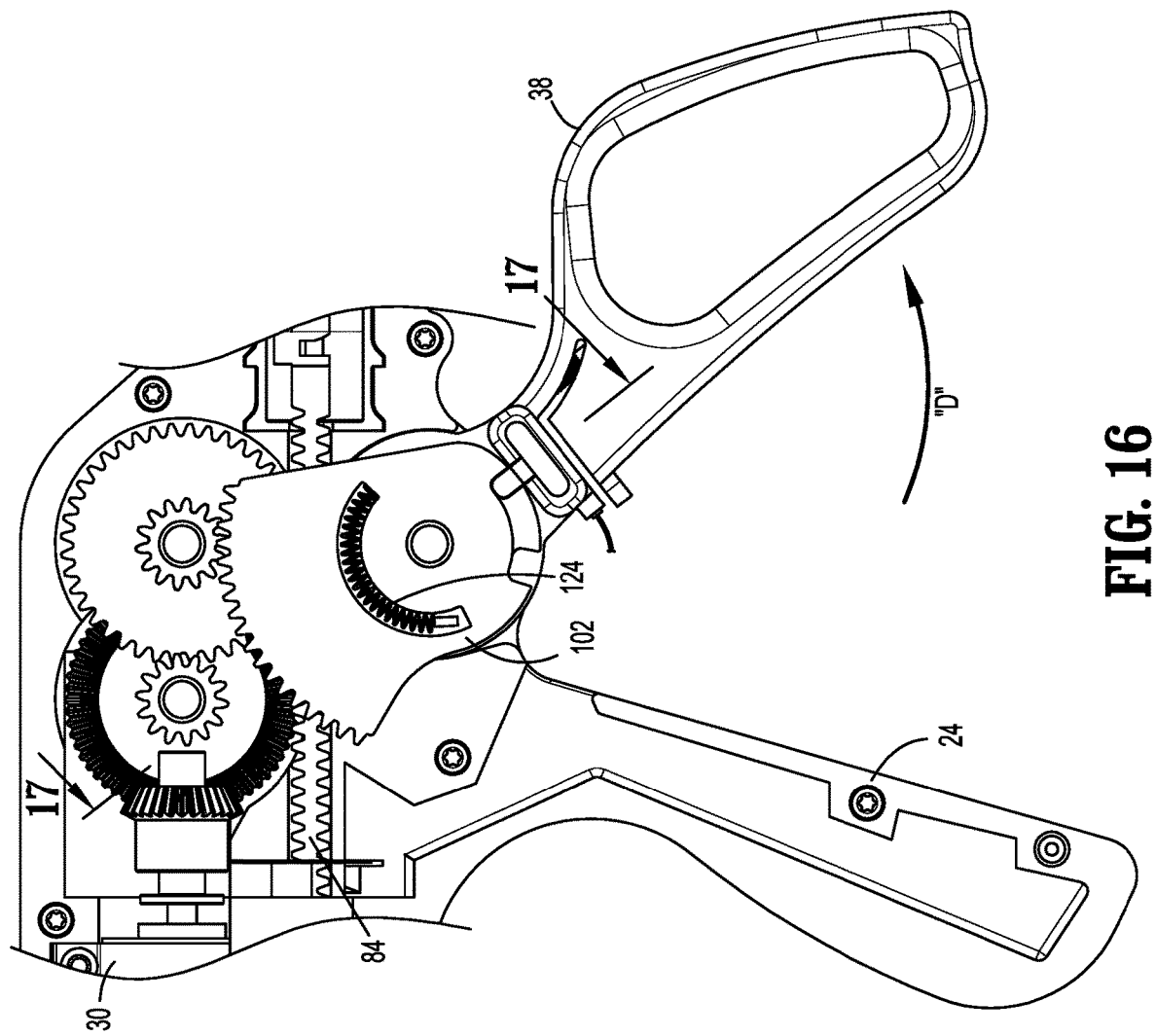
FIG. 16 is a side view illustrating the trigger assembly in a staple fire ready state.

With reference to FIGS. 14 and 15, while the rack 84 is being translated by the manual actuation of the trigger 38 and the assistance of the motor 30, the fire gear 102 is rotated due to the engagement between the pinion gear 78b of the second compound gear 78 and the gear teeth of the fire gear 102. However, due to the low transfer ratio between the pinion gear 78b of the second compound gear 78 and the fire gear 102, the fire gear 102 rotates at a substantially slower rate than does the trigger 38. As such, the trigger 38 rotates relative to the fire gear 102, whereby the protuberance 126 of the trigger 38 moves through the arcuate channel 122 in the fire gear 102, in the direction indicated by arrow "B" in FIG. 15, to compress the spring 124 therein.

Upon moving the trigger 38 toward the actuated position, as shown in FIG. 15, the tissue is sufficiently clamped by the end effector 20 and ready for stapling. With the trigger 38 in the actuated position, the proximal slot 120a of the fire gear 102 is aligned with the nub 110 of the button 42. If the user desires to staple the clamped tissue at this stage, prior to releasing the trigger 38 from the actuated position, the button 42 may be translated, in the direction indicated by arrow "C" in FIG. 14, from the left position, in which the nub 110 of the button 42 is received in the proximal section 112a of the slot 112 in the clamp gear 100, through the proximal slot 120a of the fire gear 102, and into the right position, in which the nub 110 of the button 42 is received in the channel 118 of the fire gear 102. The user releases the trigger 38 after moving the button 42 to the second position and the now-loaded spring 124 in the fire gear 102 drives a rotation of the trigger 38, in the direction indicated by arrow "D" in FIG. 16, back to the unactuated or starting position.

As the trigger 38 moves to the unactuated position, the nub 110 of the button 42 moves therewith and through the channel 118 of the fire gear 102. Since the nub 110 of the button 42 is free to move through the channel 118 of the fire gear 102 during the trigger 38 release, the rotation of the trigger 38 back to the unactuated position does not produce any movement of the rack 84. It is contemplated that the motor 30 may hold the rack 84 in position to maintain the end effector 20 in the clamped state throughout this process. Upon the trigger 38 moving to the unactuated position, the nub 110 of the button 42 becomes aligned with the distal slot 120b of the fire gear 102, whereby the springs 108 bias the button 42, in the direction indicated by arrow "E" in FIG. 17, to position the nub 110 of the button 42 in the distal slot 120b of the fire gear 102. With the nub 110 of the button 42 captured in the distal slot 120b of the fire gear 102, the trigger 38 and fire gear 102 are rotationally fixed to one another.

Figure 18:
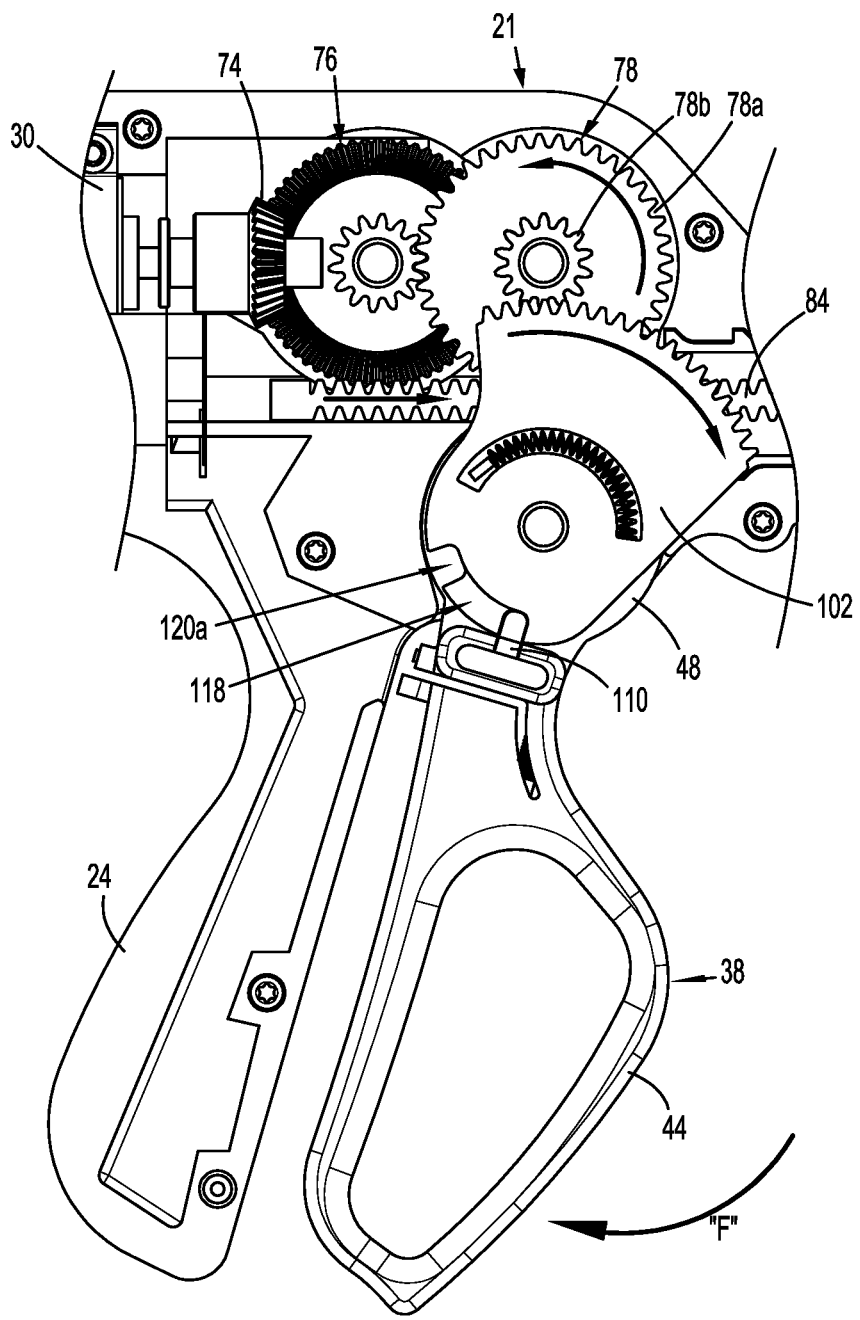
FIG. 18 is a side view illustrating the trigger assembly in the fully fired state.

To carry out the stapling function of the end effector 20, the trigger 38 is rotated toward the handle portion 24 of the handle housing 21, in the direction indicated by arrow "F" in FIG. 18, to drive a concomitant rotation of the fire gear 102. The rotation of the fire gear 102 causes the second compound gear 78 to rotate due to the engagement between the fire gear 102 and the pinion gear 78b of the second compound gear 78. The rack 84 and the attached fire rod 86 (FIG. 7) translate in response to the rotation of the second compound gear 78 to fire staples from the end effector 20. It is contemplated that the motor-assistance program may be activated at this stage in the same manner described above with respect to the clamping stage. As a result of the gear ratio between the fire gear 102 and the second compound gear 78, rotation of the fire gear 102 causes a rapid translation of the rack 84/fire rod 86 compared to when the clamp gear 100 is engaged with the trigger 38. This rapid translation of the rack 84/fire rod 86 allows for the fire rod 86 to travel the full staple distance with one full squeeze of the trigger 38 allowing for a smooth and even firing.

To reset the surgical instrument 10, the motor reverse button 33 (FIGS. 2 and 7) is actuated to move the trigger 38 distally to the unactuated position. With the trigger 38 in the unactuated position, the nub 110 of the button 42 is aligned with the distal section 112b of the slot 112 of the clamp gear 100, whereby the springs 108 (FIG. 4) of the trigger assembly 34 bias the nub 110 of the button 42 into the slot 112 of the clamp gear 100. With the button 100 engaged with the clamp gear 100, the surgical instrument 10 is set for clamping tissue. In aspects, resetting may be accomplished by a manual retraction of the trigger 38.

Any of the components described herein may be fabricated from either metals, plastics, resins, composites or the like taking into consideration strength, durability, wearability, weight, resistance to corrosion, ease of manufacturing, cost of manufacturing, and the like.

It will be understood that various modifications may be made to the embodiments of the presently disclosed surgical instruments. Therefore, the above description should not be construed as limiting, but merely as exemplifications of embodiments. Those skilled in the art will envision other modifications within the scope and spirit of the disclosure. For example, any and all features of one described embodiment may be suitably incorporated into another embodiment.

What is claimed is:

1. A handle assembly of a hand-held surgical instrument, comprising:
   a handle housing;
   a rack axially movable within the handle housing and configured to operably couple to a functional component of an end effector assembly, the rack having a bottom surface defining a first set of gear teeth and a top surface defining a second set of gear teeth;
   a trigger movably coupled to the handle housing;
   a clamp gear operably coupled to the first set of gear teeth of the rack; and
   a fire gear operably coupled to the second set of gear teeth, wherein the trigger is configured to switch between:
   a first state in which the trigger is non-rotationally coupled to the clamp gear such that an actuation of the trigger translates the rack via the clamp gear; and a second state, in which the trigger is non-rotationally coupled to the fire gear such that an actuation of the trigger translates the rack via the fire gear.

2. The handle assembly according to claim 1, further comprising a button coupled to the trigger and configured to move between a first position, in which the button non-rotationally couples the clamp gear to the trigger, such that the clamp gear rotates in response to an actuation of the trigger, and a second position, in which the button non-rotationally couples the fire gear to the trigger, such that the fire gear rotates in response to an actuation of the trigger.

3. The handle assembly according to claim 2, wherein the button includes a nub, and the clamp gear defines a slot in which the nub of the button is configured to be received when the button is in the first position.

4. The handle assembly according to claim 3, wherein the slot has a first section defining a first thickness, and a second section defining a second thickness, different than the first thickness.

5. The handle assembly according to claim 3, wherein the fire gear defines a first slot in which the nub of the button is configured to be received when the button is in the second position.

6. The handle assembly according to claim 5, wherein the fire gear defines a channel along which the nub is configured to travel, the first slot being disposed at a first end of the channel, and the fire gear defining a second slot disposed at a second end of the channel.

7. The handle assembly according to claim 6, wherein the nub of the button moves from the first position to the second position when the slot of the clamp gear is aligned with the first slot of the fire gear.

8. The handle assembly according to claim 6, wherein the trigger and the fire gear are non-rotationally coupled to one another when the nub of the button is received in the second slot of the fire gear.

9. The handle assembly according to claim 6, wherein the fire gear defines an arcuate channel having a spring received therein, and the trigger has a protuberance received in the arcuate channel, the protuberance of the trigger being configured to compress the spring in response to a movement of the trigger from an unactuated position to an actuated position.

10. The handle assembly according to claim 9, wherein the spring is configured to rotate the trigger toward the unactuated position upon the nub of the button moving from the slot of the clamp gear to the channel of the fire gear.

11. The handle assembly according to claim 2, wherein the button is resiliently biased toward the first position.

12. The handle assembly according to claim 1, wherein the fire gear defines an arcuate channel having a spring received therein, and the trigger has a protuberance received in the arcuate channel, the protuberance of the trigger being configured to compress the spring in response to a movement of the trigger from an unactuated position to an actuated position.

13. The handle assembly according to claim 1, further comprising a compound gear including:
 a spur gear in meshing engagement with the second set of teeth of the rack; and
 a pinion gear in meshing engagement with the fire gear.

14. The handle assembly according to claim 13, wherein the fire gear is a sector gear, and the clamp gear is a spur gear in meshing engagement with the first set of teeth of the rack.

15. The handle assembly according to claim 1, further comprising:

a motor disposed within the handle housing; and
a drive gear drivingly coupled to the motor and operably coupled to the rack, such that the rack is configured to axially move in response to at least one of an activation of the motor or a manual actuation of the trigger.

16. The handle assembly according to claim 15, further comprising a compound gear including:
 a spur gear operably coupled to the drive gear and in meshing engagement with the second set of teeth of the rack; and
 a pinion gear in meshing engagement with the fire gear.

17. The handle assembly according to claim 15, further comprising a sensor associated with the trigger and configured to sense a manual actuation of the trigger, wherein the motor is configured to be activated in response to the sensor sensing the manual actuation of the trigger.

18. The handle assembly according to claim 17, wherein the trigger includes:
 a handle portion; and
 a flange extending from the handle portion, the handle portion configured to deflect relative to the flange to move the sensor.

19. The handle assembly according to claim 18, wherein the sensor is a hall effector sensor attached to the handle portion or the flange, the handle assembly further comprising a magnet attached to the other of the handle portion or the flange.

20. The handle assembly according to claim 18, wherein the trigger defines a cutout allowing the handle portion to deflect relative to the flange.

21. A handle assembly of a hand-held surgical instrument, comprising:
 a handle housing;
 a rack axially movable within the handle housing and configured to operably couple to a functional component of an end effector assembly, the rack having a bottom surface defining a first set of gear teeth and a top surface defining a second set of gear teeth;
 a trigger movably coupled to the handle housing;
 a clamp gear coupled to the trigger and operably coupled to the first set of gear teeth of the rack;
 a fire gear coupled to the trigger and operably coupled to the second set of gear teeth; and
 a compound gear including:
  a spur gear in meshing engagement with the second set of teeth of the rack; and
  a pinion gear in meshing engagement with the fire gear.

22. A handle assembly of a hand-held surgical instrument, comprising:
 a handle housing;
 a rack axially movable within the handle housing and configured to operably couple to a functional component of an end effector assembly, the rack having a bottom surface defining a first set of gear teeth and a top surface defining a second set of gear teeth;
 a trigger movably coupled to the handle housing;
 a clamp gear coupled to the trigger and operably coupled to the first set of gear teeth of the rack;
 a fire gear coupled to the trigger and operably coupled to the second set of gear teeth;
 a motor disposed within the handle housing; and
 a drive gear drivingly coupled to the motor and operably coupled to the rack, such that the rack is configured to axially move in response to at least one of an activation of the motor or a manual actuation of the trigger.

* * * * *